United States Patent
Räke et al.

(10) Patent No.: US 7,905,115 B2
(45) Date of Patent: Mar. 15, 2011

(54) GLASS POWDER, ESPECIALLY BIOLOGICALLY ACTIVE GLASS POWDER, AND METHOD FOR PRODUCING GLASS POWDER, ESPECIALLY BIOLOGICALLY ACTIVE GLASS POWDER

(75) Inventors: Guido Räke, Pfaffen-Schwabheim (DE); Hildegard Römer, Florsheim (DE); Peter Schreckenberg, Bremen (DE); Josè Zimmer, Losheim am See (DE); Frank Büllesfeld, Frankfurt (DE); Jörg Fechner, Mainz (DE); Cevin Czisch, Bremen (DE); Udo Fritsching, Bremen (DE)

(73) Assignee: Schott AG, Frankfurt (DE)

( * ) Notice: Subject to any disclaimer, the term of this patent is extended or adjusted under 35 U.S.C. 154(b) by 785 days.

(21) Appl. No.: 11/813,449

(22) PCT Filed: Dec. 21, 2005

(86) PCT No.: PCT/EP2005/013792
§ 371 (c)(1),
(2), (4) Date: Sep. 27, 2007

(87) PCT Pub. No.: WO2006/072394
PCT Pub. Date: Jul. 13, 2006

(65) Prior Publication Data
US 2008/0060382 A1    Mar. 13, 2008

(30) Foreign Application Priority Data

Jan. 8, 2005  (DE) ........................ 10 2005 001 078

(51) Int. Cl.
C03B 37/06 (2006.01)

(52) U.S. Cl. .............. 65/466; 65/21.1; 65/21.2; 65/454; 65/462; 65/465; 65/524; 65/525; 65/526; 264/12

(58) Field of Classification Search ................ 65/21.1, 65/21.2, 454, 462, 465, 466, 524, 525, 526; 264/12
See application file for complete search history.

(56) References Cited

U.S. PATENT DOCUMENTS

| | | | |
|---|---|---|---|
| 4,386,896 A | 6/1983 | Ray | 425/7 |
| 4,472,329 A * | 9/1984 | Muschelknautz et al. | 264/12 |
| 4,851,046 A | 7/1989 | Low et al. | 106/35 |
| 5,074,916 A | 12/1991 | Hench et al. | 106/35 |
| 5,855,965 A * | 1/1999 | Molerus et al. | 427/475 |

(Continued)

FOREIGN PATENT DOCUMENTS
DE    10002394    5/2001
(Continued)

OTHER PUBLICATIONS
DE 10002394 (Machine Translation) [online], [retrieved on May 19, 2010], retrieved from EPO Database (http://ep.espacenet.com/advancedSearch?locale=en_EP).*

(Continued)

Primary Examiner — Matthew J Daniels
Assistant Examiner — Yana Belyaev
(74) Attorney, Agent, or Firm — Taylor IP

(57) ABSTRACT

The invention relates to glass powder, especially a biologically active glass powder, which includes a plurality of glass particles and which is characterized by the following features: the glass particles are made up by >90% of non-spherical particles; the geometry of the individual non-spherical particle is characterized by a ratio of length to diameter of 1.1 to $10^5$.

20 Claims, 8 Drawing Sheets

U.S. PATENT DOCUMENTS

| | | | | |
|---|---|---|---|---|
| 6,086,374 | A | 7/2000 | Litkowski et al. | 433/217.1 |
| 6,167,729 | B1 | 1/2001 | Watton et al. | 65/497 |
| 6,190,643 | B1 | 2/2001 | Stoor et al. | 424/49 |
| 6,444,009 | B1 * | 9/2002 | Liu et al. | 75/332 |
| 6,475,631 | B1 * | 11/2002 | Yamamoto et al. | 428/480 |
| 2003/0118658 | A1 * | 6/2003 | Trogolo et al. | 424/490 |

FOREIGN PATENT DOCUMENTS

| | | | |
|---|---|---|---|
| DE | 10002394 | * | 10/2001 |
| EP | 0017723 | * | 10/1980 |
| EP | 1360152 | | 11/2003 |
| WO | WO 98/12116 | | 3/1998 |
| WO | WO03/018499 | | 3/2003 |
| WO | WO 03018499 | * | 3/2003 |

OTHER PUBLICATIONS

WO 03018499 (Machine Translation) [online], [retrieved on May 19, 2010], retrieved from EPO Database (http://ep.espacenet.com/advancedSearch?locale=en_EP).*

International Written Opinion for PCT/EP2005/013792.

International Preliminary Report for PCT/EP2005/013792.

* cited by examiner

Viscosity from Example 1 and 2:

Viscosity of Glass from Example 4:

Viscosity of Glass from Example 7:

Primary gas

Secondary gas

Spray

REM-picture of fibers from Experiment 3

GLASS POWDER, ESPECIALLY BIOLOGICALLY ACTIVE GLASS POWDER, AND METHOD FOR PRODUCING GLASS POWDER, ESPECIALLY BIOLOGICALLY ACTIVE GLASS POWDER

BACKGROUND OF THE INVENTION

1. Field of the Invention

The invention relates to glass powder, especially biologically active glass powder, and a method to produce glass powder, especially biologically active glass powder.

2. Description of the Related Art

Biologically active glass powders in the form of bio-active glass powders are already known from U.S. Pat. No. 5,074,916 and in the form of anti-microbial active glass powders from WO 03/018499. The glass powders include a plurality of glass particles of any shape including spherical as well as non-spherical particles, for example in the form of glass fibers. The production of particles of this type may occur in different methods, whereby the glass is generally melted and converted to a semi-finished state or to ribbons which are then ground to a certain granular size. It has been demonstrated that the biological effectiveness is greatly dependent upon the particle size which manifests in an accordingly high degree of grinding.

Methods for producing particles from a melt, especially from a mineral or glass melt are known in a plurality of implementations. For example, in one of the methods for the production of glass wool for insulating purposes which is described in documentation EP 13 60 152 and EP 09 31 027 the glass melt is put into a rotating drum which is equipped with small diameter holes that are located in the wall which forms the surface area. Due to the centrifugal forces the glass melt is forced through the small holes. A significant disadvantage associated with the use of rotating elements of this type is that they are subjected to especially high wear and tear in the hot area due to the necessarily high rotational speed, thereby providing only a relatively low life span of such units.

A method for producing metallic glass powders is already known from U.S. Pat. No. 4,386,896. In this method, the glass melt is atomized under the influence of moving elements and a gas and is directed toward a centrifuge disk. The described atomizing methods include a single substance nozzle as well as the use of cold gas. Also in this scenario the mechanical elements of the apparatus which are necessary for the atomization are also exposed to the high temperatures of the glass melt, resulting in high maintenance of this type of apparatus. In addition, the throughput is determined by the speed of the motion and the rotational speed of the rotating elements.

A method for atomizing of metal melts which utilizes two nozzles in the atomization area is described in WO 98/12116. Here, a first nozzle unit is utilized for atomizing and a second nozzle for providing the cold gas in order to cool the created droplets. In contrast, DE 100 02 394 C1 discloses a method for the atomization of melts utilizing hot gas in order to produce spherical particles. Here, a melt having a dynamic viscosity $\eta$ in the range between 0.01 and 100 Ns/m² is produced. The molten stream is atomized utilizing a primary gas, whereby the primary gas has a temperature of at least $T_A = T_G$ $T_G$=Glass forming temperature
$T_A$=Glass exit temperature at the nozzle discharge point. Cooling of the particles which were formed during atomizing occurs in a cooling zone downstream from the nozzle in the production flow through utilization of a quenching medium, whereby the temperature of the quenching medium is lower than the temperature of the glass forming temperature. In this method the glass melt stream is led over a certain distance and the primary gas is supplied through several individual nozzles. This supply method over a long period of time avoids cooling and favors the formation of spherical particles. Particles of this type however, do not fulfill the demands put upon biologically active glasses which must be characterized by a high biological effectiveness.

What is needed in the art is to develop a glass powder, especially a biologically highly active glass powder, as well as a method to produce a glass powder, especially a biologically highly active glass powder which is characterized by a high throughput combined with low thermal and mechanical demand upon the elements which are associated with the particle formation, as well as by a favorable energy balance. The construction and controls related expenditure should be kept as low as possible.

SUMMARY OF THE INVENTION

The inventors recognized that the biological effectiveness is determined primarily by the particle size, especially by the surface that is available for reactions. The inventive biologically active glass powder includes a plurality of non-spherical glass particles. The share of the non-spherical glass particles relative to a predetermined total volume of particles is preferably higher than 70%, preferably higher than 80%. The geometry of the individual non-spherical particle is provided by a ratio of length to diameter of 1.1 to $10^5$, preferably 100 to $10^4$, especially preferably of 10 to $10^4$.

The described particle geometry provides a substantial surface enlargement of a predefined amount of glass powder, especially biologically active glass powder when compared with the same amount of glass powder having spherical particles, resulting especially in the availability of a larger effective reactive surface for biological processes and reactions.

The length of the individual glass particle is approximately 1 µm to $10^5$ µm, preferably 10 µm to $10^4$ µm, especially preferably 100 µm to $10^4$ µm.

Fibers are characterized by a diameter in the range of 0.5 µm to 10 µm, preferably 0.5 µm to 2 µm.

Bio-active as well as antimicrobial glass powders are sub-summarized under biologically active glass powders. In the case of bioactive glass powders the glass of the glass powder includes the following components:

| | |
|---|---|
| $SiO_2$ | 40-70 weight % |
| $P_2O_5$ | 2-15 weight % |
| $Na_2O$ | 0-35 weight % |
| CaO | 5-35 weight % |
| MgO | 0-15 weight % |
| F | 0-10 weight % |

Bioactive glass differs from conventional lime-sodium-silicate glasses in that it is not rejected by the body. The designation "bioactive" describes a glass which forms a firm connection with body tissue, thereby forming a hydroxylapatite layer. These types of glass powders display a biocidal or biostatic effect vis-à-vis bacteria, fungi and viruses. In contact with humans they are skin tolerant, toxicologically harmless.

In a biologically active glass powder in the form of an antimicrobial active glass powder the glass of the glass powder includes the following components:

| | |
|---|---|
| $P_2O_5$ | 0-80 weight % |
| $SO_3$ | 0-40 weight % |
| $B_2O_3$ | 0-50 weight % |
| $Al_2O_3$ | 0-10 weight % |
| $SiO_2$ | 0-10 weight % |
| $Li_2O$ | 0-25 weight % |
| $Na_2O$ | 0-20 weight % |
| $K_2O$ | 0-25 weight % |
| CaO | 0-25 weight % |
| MgO | 0-15 weight % |
| SrO | 0-15 weight % |
| BaO | 0-15 weight % |
| ZnO | 0-25 weight % |
| $Ag_2O$ | 0-5 weight % |
| CuO | 0-10 weight % |
| $GeO_2$ | 0-10 weight % |
| $TeO_2$ | 0-15 weight % |
| $Cr_2O_3$ | 0-10 weight % |
| J | 0-10 weight % | whereby

The sum $SiO_2+P_2O_5+B_2O_3+Al_2O_3$ amounts to between 30-80 weight % and the sum $ZnO+Ag_2O+CuO+GeO_2+TeO_2+Cr_2O_3+J$ amounts to 0.1-40 weight % and the sum $R^1_2O+R^2O$ amounts to 0.1-60% weight whereby $R^1$ is an alkali metal and $R^2$ is an earth alkali metal.

In the case of antimicrobial glasses, especially glass powders from antimicrobial glasses, alkalis of the glass are exchanged with H+-ions of the aqueous medium due to reactions on the surface of the glass powder. The antimicrobial action of the ion exchange is based, among other factors, on an increase of the pH value and the osmotic effect upon micro-organisms. Based on increased pH value due to ion exchange between one metal ion, for example an alkali or earth alkali metal ion and the $H^+$ ions of the aqueous solution, as well as due to an ion-contingent limitation of cell growth (osmotic pressure, interruption of metabolic processes of the cells) glass powders of this type react antimicrobial in aqueous mediums.

With all the previously listed glass powders $Na_2O$ is utilized as a fluxing agent during melting of the glass. At concentrations <5%, the melting characteristics are influenced negatively. In addition, the necessary mechanism of the ion exchange is no longer sufficient to achieve the antimicrobial effect.

Alkali and earth alkali oxides may especially be added in order to increase the ion exchange, thereby intensifying the antimicrobial effect. The amount of $Al_2O_3$ which may be added to enhance the chemical constancy of the crystallization stability as well as the control of the antimicrobial effect is max 10 weight %.

$B_2O_3$ functions as a network creator and may also aid the control of the antimicrobial effect.

ZnO is an essential component for hot-forming characteristics of the glass. It improves the crystallization stabilities and increases the surface tension. In addition, it can support the antimicrobial effect. Low $SiO_2$ contents increase the crystallization stability. In order to achieve an antimicrobial effect as much as 25 weight % should be contained.

In accordance with the current invention the method for producing glass powder, especially biologically active glass powder including non-spherical particles can be sub-divided essentially into two categories. In a first method a glass melt (which can also be referred to as a melt, a molten mass or a molten glass mass) is produced, followed by the particle formation or fiber formation. Methods are selected for the particle formation which distinguish themselves through a low constructive and manufacturing expenditure and which especially assure a high throughput at a favorable energy balance. According to a first design the particle formation occurs through granulation from the melt. This occurs due to an intense shear effect upon the free-flowing glass stream and appropriate cooling. The granules which are created by this granulation are characterized by a large size and therefore a small surface. Particles having a diameter of 0.5 μm to 10 μm and a length of 2 to $10^5$ μm are created. Shaping may be fiber like as well as irregular. Granulation can be followed by a grinding process. In the process of this the particles are reduced to a size of 0.5 to 8 μm diameter and a length of 2 to 100 μm. Irregularly formed particles which as a rule are not formed spherically, result again from the also irregularly formed particles.

In accordance with an especially advantageous design form the formation of the glass particles fundamental to the grinding process occurs through an atomizing process. This ensures that predominantly non-spherical particles, especially fibers, are available as starting material for the subsequent grinding process. The still hot glass melt, preferably at a temperature of between 1400-1800K is being atomized by way of a gas whereby atomizing occurs preferably directly from the discharge nozzle at the discharge or transfer area of the melting zone to the atomizing zone. Two nozzles are essentially utilized for the atomization, whereby the first nozzle serves to direct the glass melt while the second nozzle initiates the actual atomization process. Through synchronization of the individual process parameters with each other the final structure can be extensively influenced, especially the particle geometry which is already available for the optional grinding process. In order to operate at a high throughput the atomization of the glass melt occurs at a high temperature. Consequently the glass melt is supplied to the atomizing area at a low viscosity. In addition the atomizing process is established largely by the process parameters in the atomizing zone which are determined by the temperature of the supplied glass and the prevailing pressure conditions. Any inert or dry gases can be used as atomizing gas. Preferred is dry nitrogen.

A gas having a low temperature, especially cold gas at a temperature of 70K to 600K, preferably 200K to 500K, especially preferably 250-400K is preferably utilized as atomizing gas. The cold gas on the one hand has a cooling effect on the glass melt, thereby providing it with a higher level of viscosity.

At the same time shear forces are transferred to the glass through the gas resulting in irregularly formed particles, especially fibers.

The atomization process can also feasibly be accomplished through atomizing by way of hot gas. In this scenario the gas is then supplied at a temperature of between 500 and 1300K, preferably 700 to 1230K. A pressure of between 0.2 and 0.5, preferably 0.34 MPa is applied in the atomization zone.

The atomization process then occurs preferably in the area of entry of the glass melt into the atomization area. Atomization occurs preferably by way of a nozzle arrangement which provides a planiform effect upon the molten stream whereby the atomization area is kept relatively short in order to achieve quick cooling while creating irregularly formed particles. Cooling can occur directly through the supply of an appropriate gas or quenching medium or indirectly, that is without the active influence of additional measures.

Particle sizes, especially lengths of 2-100 μm can be achieved in the subsequent grinding process. Particle sizes of 2-10 μm have proven to be especially advantageous. The grinding process itself may be conducted dry or also with the assistance of aqueous or non-aqueous grinding media.

The inventive method utilizes preferably a hot gas atomization arrangement. This includes a melting apparatus representing a melting zone, as well as an atomization apparatus representing the atomization zone, whereby the melting apparatus is connected with the atomization apparatus. The atomization apparatus includes two nozzles which are allocated to the glass melt, especially to the glass melt stream and through which a gaseous medium acts upon the glass melt stream. The glass melt stream itself is preferably delivered through an opening which is preferably located in the direction of gravitation, or through a nozzle, into the atomization zone of the atomization apparatus. The atomization zone can be sub-divided into two sections—a first section where the glass melt, especially the glass melt jet being emitted from the opening or the nozzle is still directed in the direction of gravitation, and a second section which is characterized by the effect of the gaseous medium which is used for atomizing upon the glass melt jet. In this arrangement a first nozzle for the inlet of a gaseous medium is allocated to the discharge nozzle in order to direct the molten jet. This is preferably in the embodiment of an annular gap and is located coaxially to the discharge opening of the first nozzle. Arrangements which are equipped with a plurality of individual nozzles which are located symmetrically around the circumference of the molten jet are also feasible. The second nozzle is designed such that the gaseous medium impinges upon the molten jet at an angle, whereby an angle range of between 20° and 60°, preferably of 40 to 60°, especially preferably of 45° is selected. The second nozzle is designed so that the impingement occurs planiform or linear uniformly in circumferential direction, specific to the surface of the molten jet and also without interruptions. With regard to the direction of discharge the first nozzle is located parallel to molten glass jet. The second jet is located downstream from the first jet and is aligned at an angle to said first jet. Atomization occurs preferably in an area of the emission from the discharge opening, that is the discharge nozzle and therefore in the initial area of the atomization zone. Due to the then occurring cooling particles having an irregular geometry are formed, preferably in fiber form. In addition these can be further cooled in a downstream cooling device. As a rule the particles which were formed in the atomization zone are further transported over a distance of approx. 1 m and are only then subjected to a cooling process. This can be in the form of a liquid bath or through the addition of an inflowing gaseous medium.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

Corresponding reference characters indicate corresponding parts throughout the several views. The exemplifications set out herein illustrate embodiments of the invention, and such exemplifications are not to be construed as limiting the scope of the invention in any manner.

DETAILED DESCRIPTION OF THE INVENTION

Figure 1A:
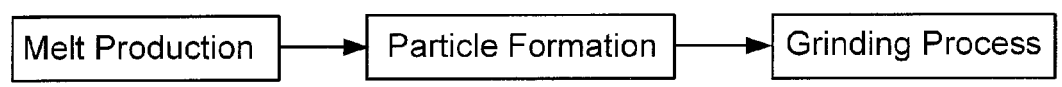
FIGS. 1a-1c show signal flow diagrams which illustrate in schematically simplified depiction the basic sequence of the inventive process.
Figure 1B:
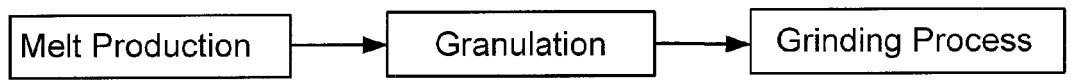
Figure 1C:
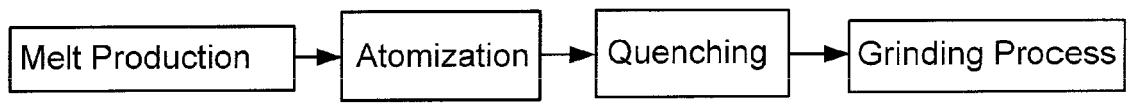

Referring now to the drawings, and more particularly to FIGS. 1a-1c, there is shown signal flow diagrams which illustrate in schematically simplified depiction the basic principle of the inventive method to produce non-spherical glass particles, especially from biologically active glass. The biologically active glasses include the so-called bioactive glasses which are characterized by the following glass composition ranges:

| | | |
|---|---|---|
| $SiO_2$ | 40-70 | weight % |
| $P_2O_5$ | 2-15 | weight % |
| $Na_2O$ | 0-35 | weight % |
| CaO | 5-35 | weight % |
| MgO | 0-15 | weight % |
| F | 0-10 | weight % | as well as antimicrobial glasses which are characterized by the following glass composition:

| | | |
|---|---|---|
| $P_2O_5$ | 0-80 | weight % |
| $SO_3$ | 0-40 | weight % |
| $B_2O_3$ | 0-50 | weight % |
| $Al_2O_3$ | 0-10 | weight % |
| $SiO_2$ | 0-10 | weight % |
| $Li_2O$ | 0-25 | weight % |
| $Na_2O$ | 0-20 | weight % |
| $K_2O$ | 0-25 | weight % |
| CaO | 0-25 | weight % |
| MgO | 0-15 | weight % |
| SrO | 0-15 | weight % |
| BaO | 0-15 | weight % |
| ZnO | 0-25 | weight % |
| $Ag2O$ | 0-5 | weight % |
| CuO | 0-10 | weight % |
| $GeO_2$ | 0-10 | weight % |
| $TeO_2$ | 0-15 | weight % |
| $Cr_2O_3$ | 0-10 | weight % |
| J | 0-10 | weight % | whereby
$SiO_2+P_2O_5+B_2O_3+Al_2O_3$ is between 30-80 weight %
and the sum
$ZnO+Ag_2O+CuO+GeO_2+TeO_2+Cr_2O_3+J$ is between 0.1-40 weight %
and
$R_2O+RO$ is between 0.1-60% weight whereby R is an alkali metal or an earth alkali metal.

In the case of antimicrobial glasses, especially glass powders from antimicrobial glasses, alkalis of the glass are exchanged with H+-ions of the aqueous medium due to reactions on the surface of the glass powder. The antimicrobial action of the ion exchange is based, among other factors, on an increase of the pH value and the osmotic effect upon micro-organisms.

In a first process step the glass is subjected to a melting process. In this process a glass melt having a high temperature, preferably in the range of 1400 to 1800K, especially preferably 1800K is produced. In the second process step the particle formation or fiber formation occurs. This can be followed by a third process step which is a grinding process. This is however not imperative. Already, the particle formation process in the second process step which occurs for example through granulation/fiber production due to shear effects from the free flowing glass stream, and appropriate cooling produces particles having a diameter of 0.5 μm-10 μm and a length of $2\text{-}10^5$ μm. Said particles already possess a surface structure large enough that they can be used as biologically highly active glass without having to undergo an additional grinding process. A grinding process following the particle formation process essentially permits non-spherical particles of a certain size in the range of 0.5 μm-8 μm and a length of 2-100 μm to be produced. Specific to a predefined volume of starting glass a share of >90% of non-spherical particles is strived for. Non-spherical particles are understood to be all achievable geometric shapes, preferably fibers, however, with the exception of spherical particles. Particle formation may occur in various ways.

According to FIG. 1*b* the particle formation occurs generally through granulation from the melt. The process includes quick cooling of a liquid glass melt in a water bath or a gas, allowing solid material granules to be formed. These solid material granules are then subjected to a grinding process. The particles formed in this process may vary. On the one hand, they may be spherical particles, or on the other hand non-spherical particles, whereby however in both instances the non-spherical particles are produced by the optional subsequent grinding process.

An especially preferred option to produce almost exclusively non-spherical particles is illustrated in FIG. 1*c* in a schematic summarization of the process steps. This particle formation process includes atomization or pulverization by use of gas. Depending upon the configuration, a cooling process for the particles which were produced during atomization may be implemented prior to the grinding process. The non-spherical particles which are available following the grinding process are characterized by a larger active surface at the identical glass volume when compared with the spherical particles. This translates for example, to a greater biological effectiveness.

FIG. 2 illustrates one implementation of a method according to FIG. 1*c*, whereby the particle formation occurs essentially through pulverization or atomization. Here, two nozzles located in tandem in the direction of the melt stream flow are utilized. Said nozzles direct the gas flows so that a return of the melt is avoided. In this scenario the melt stream is directed by the gas flowing from the first nozzle and is atomized by the gas which flows from the second successive nozzle. The two process steps—producing the melt and particle formation—are realized in a hot gas atomizing apparatus 1. With regard to the implementation of the individual process steps said apparatus is sectioned into different zones which are characterized by the individual devices implementing this function. In this example the hot gas atomization apparatus 1 includes one melting zone 2, one atomization zone 3 as well as one cooling zone 4 which, in a preferred embodiment is also followed by a separation zone 5. A melting apparatus 6 is provided in the melting zone 2. This generally includes a device 7—a receptacle for glass—in the embodiment of a pot or a trough. This device 7 is assigned to a heating device 8 which may, for example, be in the embodiment of an induction heater or an induction furnace. In this context the glass is heated in the melting apparatus 6. Due to the temperature increase said glass becomes soft and the viscosity is reduced. Examples of the temperature dependency of the glass viscosity are given in FIGS. 3*a* through 3*c* for various glass compositions according to Table 2 of this application. FIG. 3*a* illustrates the viscosity-/temperature characteristic for a glass composition according to design example 1 in Table 2. This is identified with the reference number 100. The viscosity-/temperature characteristic for a glass composition according to design example 2 in Table 2 is identified with the reference number 110.

FIG. 3*b* illustrates the viscosity-/temperature characteristic for a glass composition according to design example 4 in Table 2. This is identified with the reference number 120.

FIG. 3*c* illustrates the viscosity-/temperature characteristic for a glass composition according to design example 7 in Table 2. This is identified with the reference number 130. It is apparent that the viscosity is reduced with increasing temperature of the glass melt 9 (which can also be referred to as a melt, a molten mass, or a molten glass mass) which results from the heating process of the biologically active glass. The glass melt 9 then comes into the atomizing apparatus 10 which forms the atomizing zone 3. There may be variations in the configuration of the atomizing apparatus 10 depending on how the glass melt 9 is directed. This applies particularly to the configuration and especially to the orientation and the geometry of the discharge nozzle 11 for the glass melt and the nozzles 12 and 13 which direct the gas flows which influence the glass melt 9. In accordance with the invention two nozzles are provided which affect the glass melt in this instance nozzles 12 and 13. With the atomizing zone 3 oriented in the direction of gravity these are located following each other in down stream direction of the glass melt flow. The second nozzle 13 which is known as the so-called secondary nozzle serves to atomize the glass melt 9 while the gas flow through the nozzle 12 which is located prior to said second nozzle is utilized to prevent a return of the droplets or fibers which were created by the atomization into the atomization zone and to prevent wetting and clogging of the discharge or atomizer nozzle 11 and of the guide devices located upstream from it. The atomizer apparatus 10 is connected with the melting apparatus 6 via a guide device 14 which includes preferably a so-called Pt-guide tube which is located at the bottom end of the pot or trough and which discharges into the atomizer nozzle. The gas to influence the glass melt 9 in the atomizing zone 3 is provided by a gas supply unit 15. Preferably this unit includes a gas pre-heating device 16, especially a propane gas burner to which the gas which is to be heated is supplied. The gas pre-heating device 16 is connected with a gas tank 17 which is indicated only schematically in the drawing and which contains the gas which is to be heated, whereby the pre-heating device 16 is also connected with the atomizer apparatus 10. Inert gases are used as atomizing gases, for example nitrogen. The gas is blown into the melt, especially the glass melt 9, thus leading to atomization. The specific design and arrangement of the atomizing zone 3 is illustrated in an example of a gravity arrangement in FIG. 4. Both nozzles 12, 13 for the primary gas, in other words for the gas that is effective in the atomizing zone 3 are shown. The particle stream which is formed downstream from the nozzle 13 then reaches the cooling zone 4. A second gas and/or water is utilized as a quenching medium. The second gas may be a liquefied gas. The quenching medium can be blown in against the direction of the particle stream flow, in the direction of nozzle 13. It is however also possible to add the quenching medium for directing the particle stream in the direction of flow or at an angle.

Additional nozzles are provided to blow in the quenching medium. A bath consisting of liquefied gas or water can also be provided as quenching medium. The particles from the atomizing zone 3 then drop into the cooling zone 4 and are subsequently removed. Particles which are moved along by the gas flow are separated from the gas flow in a separator 18 in the embodiment of a cyclone separator. As an option the hereby produced particles may be supplied to a grinding device which is illustrated here only as a black box 19. The relevant particles are then subjected again to a mechanical process so that particles having a diameter of 0.5-10 µm and a length of 2-100 µm are created.

Figure 2:
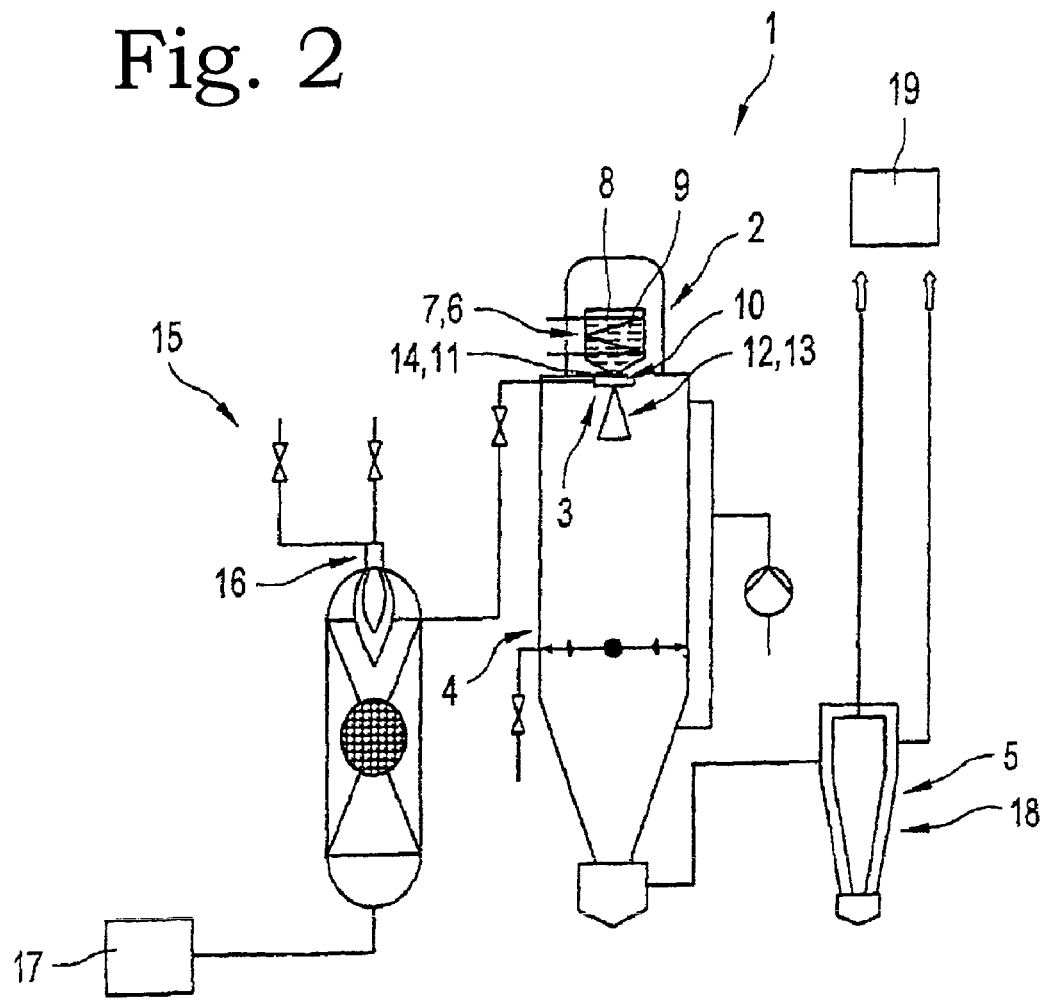
FIG. 2 shows a schematically simplified depiction of a hot gas atomizing apparatus which illustrates inventive implementations of the method according to FIG. 1c.
Figure 3A:
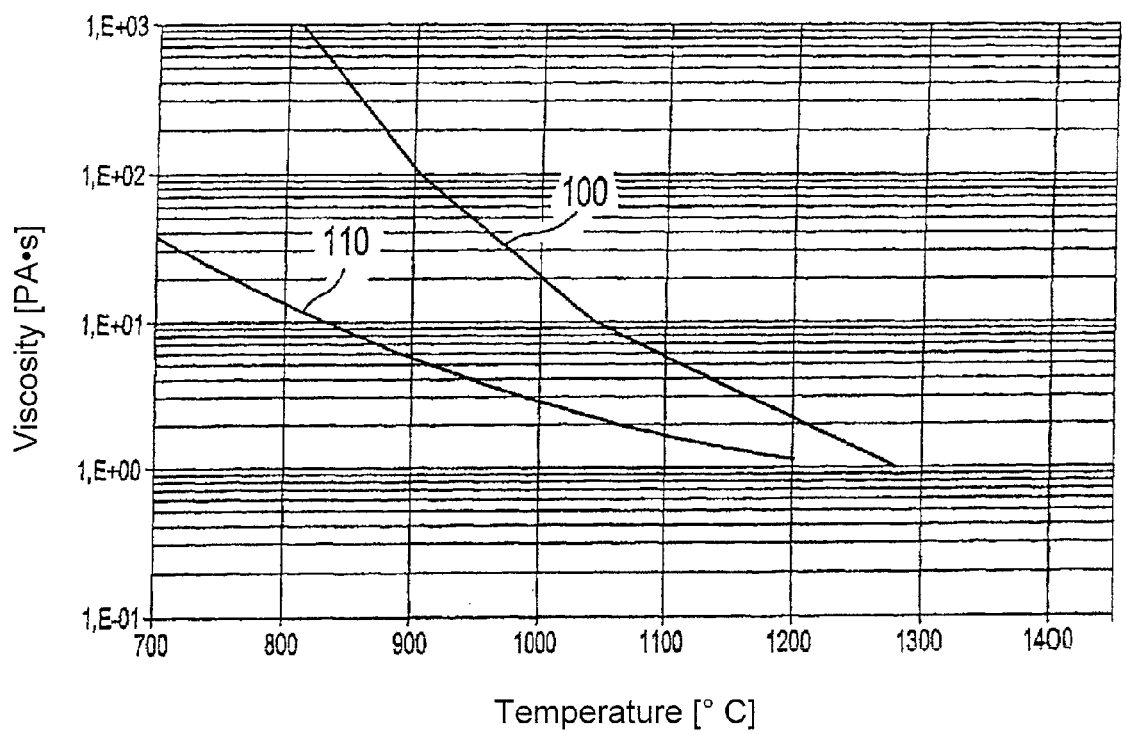
FIGS. 3a-3c show a schematically simplified depiction of the viscosity characteristics of the melt relative to the temperature of the melt for various glass compositions.
Figure 3B:
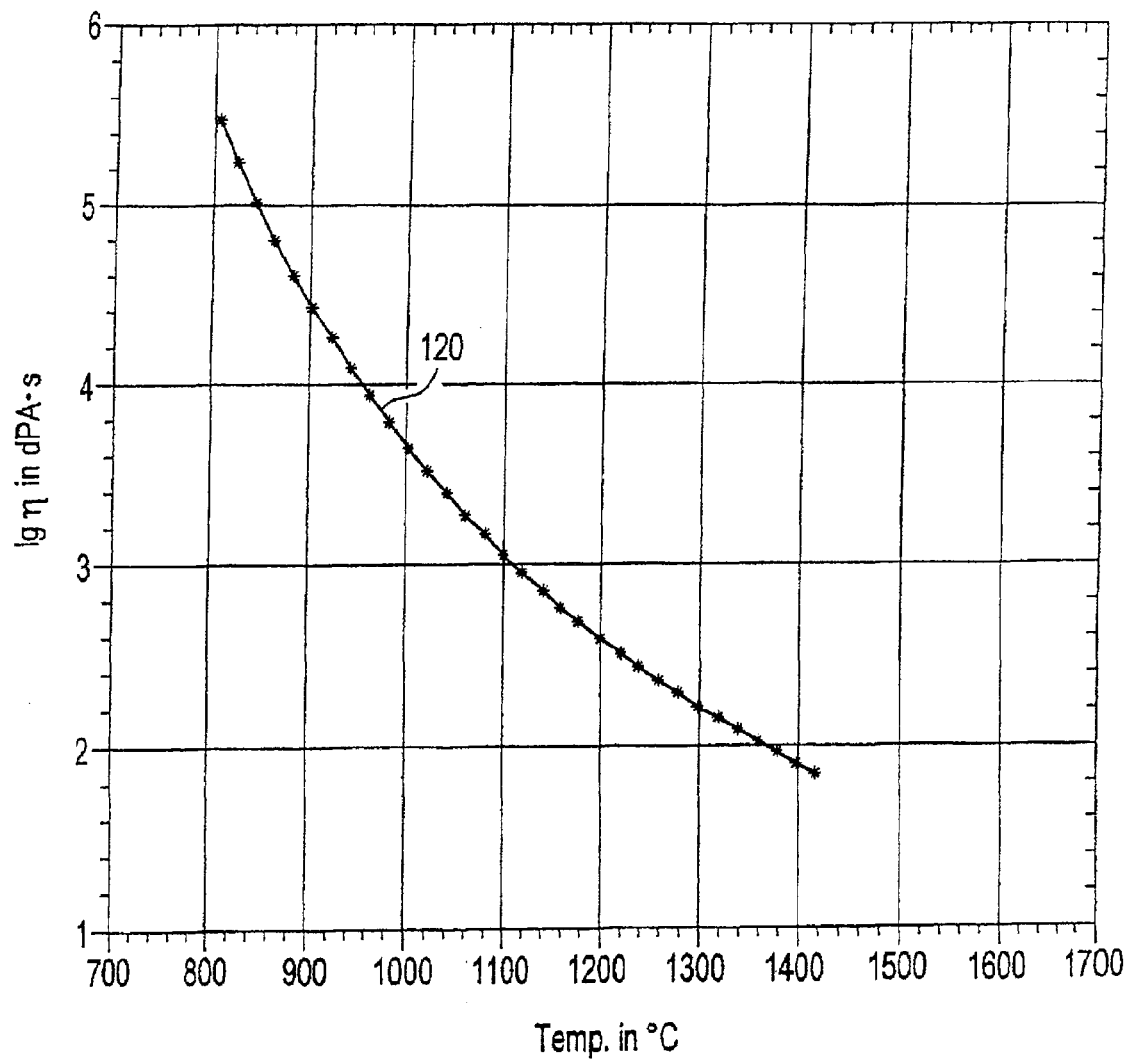
Figure 3C:
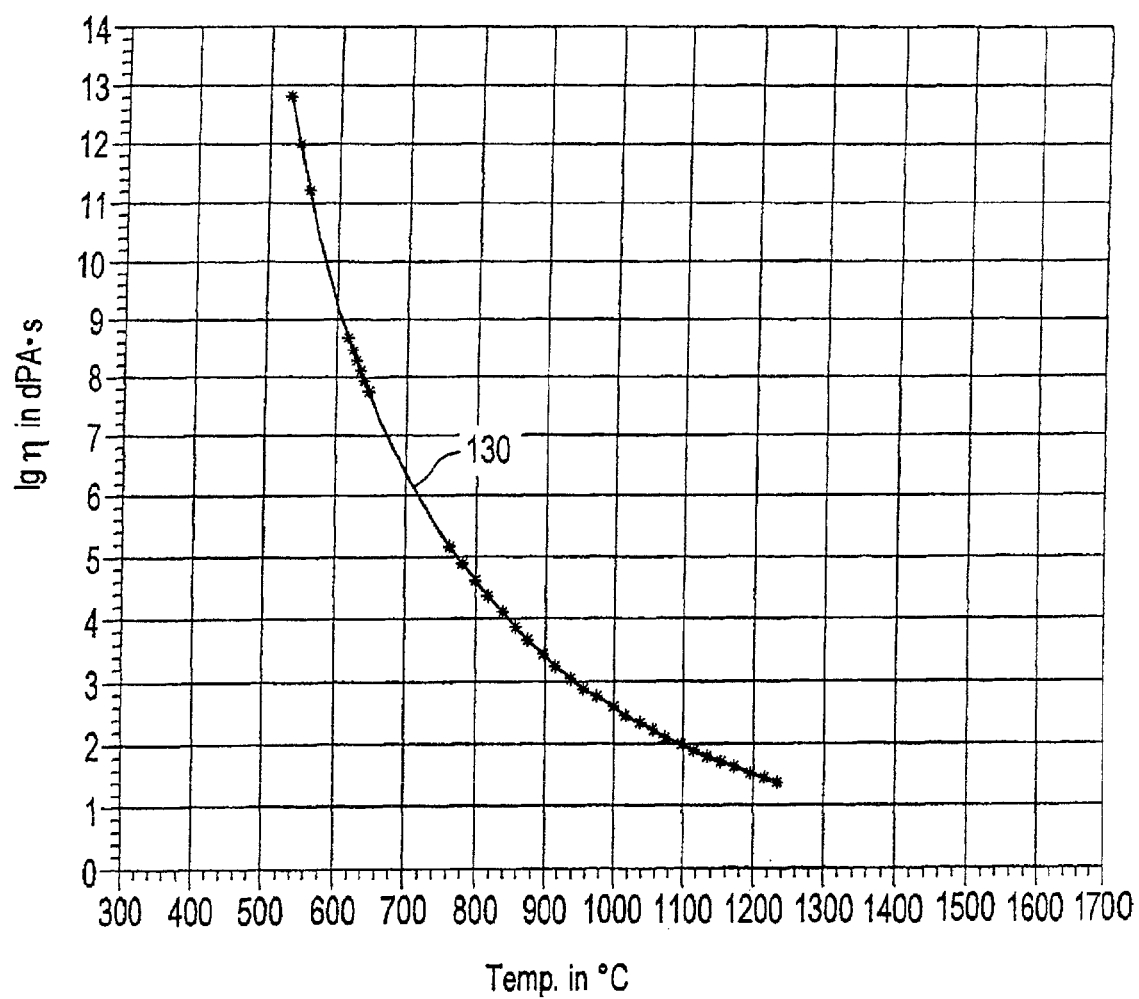
Figure 4:
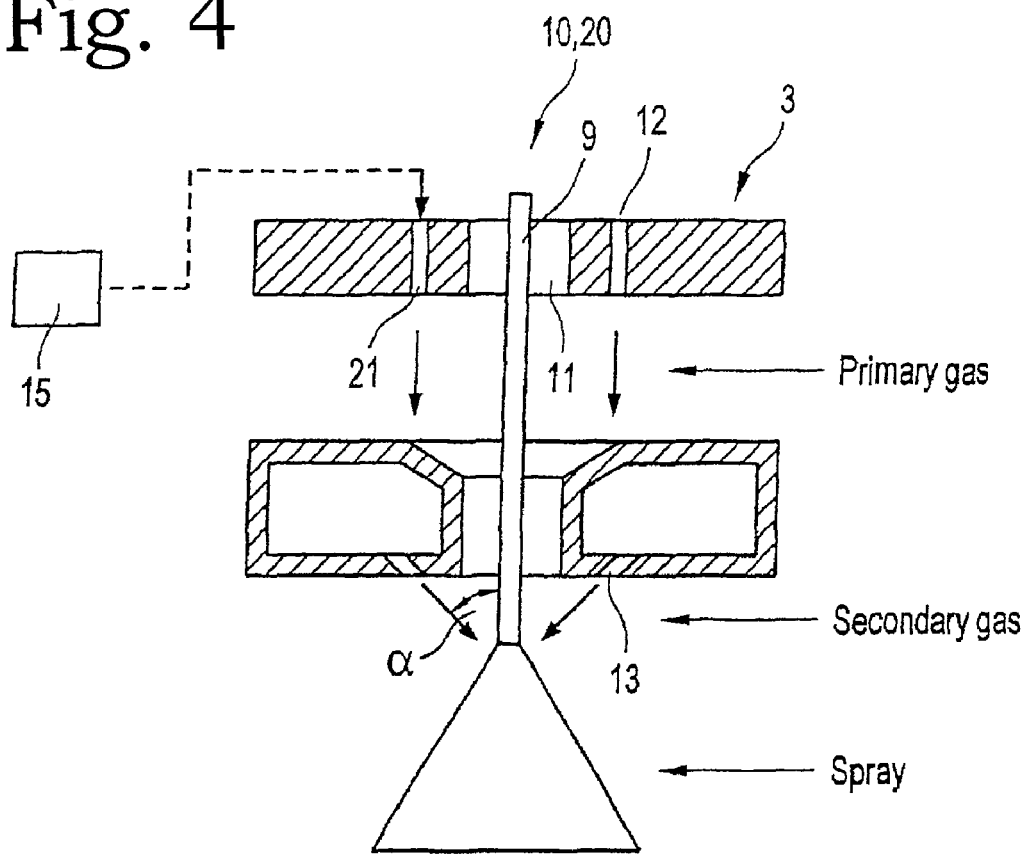
FIG. 4 shows a schematically simplified depiction of the inventive process for producing particles in a gravity-type atomizer.
Figure 5A:
FIGS. 5a-5c illustrate the resulting fibers according to the individual design examples according to Table 1 with the assistance of Rem-pictures (scanning electron microscope picture)
Figure 5B:
Figure 5C:
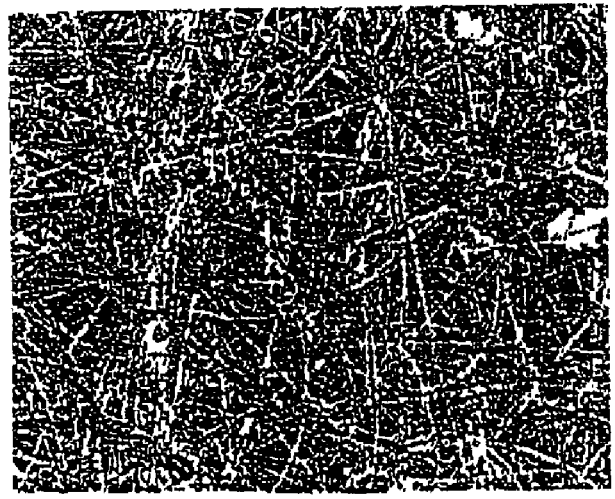
Figure 6:
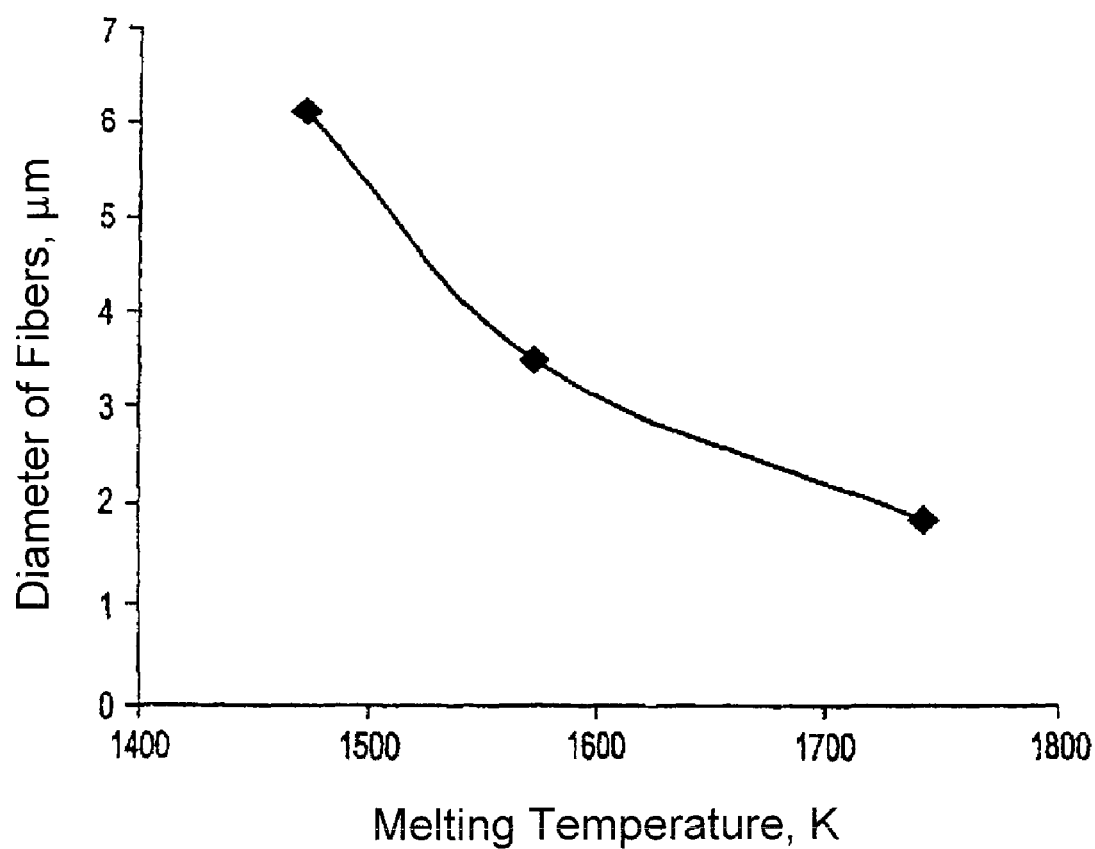
FIG. 6 illustrates the change of the resulting fiber diameters during cold gas atomization at various melting temperatures.

FIG. 4 again schematically illustrates the function of the atomizer apparatus 10 in the embodiment of a gravity atomizer 20 by depicting a segment of the illustration in FIG. 2 of the hot gas atomizer apparatus 1. Clearly shown is the discharge nozzle 11 which is preferably in the embodiment of a concentric nozzle and from which the glass melt 9 is expelled in gravity direction. The gas supply device 15 is connected with said nozzle whereby the gas emerging from this device exits through an annular gap 21 which is configured coaxially to the nozzle 11 where the glass melt jet is released and which approximately surrounds said nozzle in circumferential direction. The annular gap 21 is located in the area of the discharge opening or discharge nozzle 11 which releases the glass melt 9. This first nozzle 12 which is formed by the annular gap 21 is designed such that the gas jet discharges through this nozzle 12 parallel to the glass melt stream 9. In this configuration the gas can flow over the entire circumferential direction in the annular gap or at least over a section. It is however critical that a guiding function for the glass melt 9 is achieved through the gas which is directed via the first nozzle 12. The glass melt stream 9 which is herewith directed in vertical direction is then subjected to the gas flow of the second nozzle 13. This nozzle is configured such that the gas discharges at an angle of approx. 20-60°, preferably approximately 45° in the direction toward the glass melt 9, especially the melt jet. This melt jet is being atomized through the influence of the gas which is ejected through the second nozzle 13 and which is preferably also supplied through the gas supply device 15. It is preferred if the same gas is always supplied to the first and the second nozzle 12, 13. The atomizing effect is thereby essentially determined by the emission speed of the melt stream 9 or the melt jet from the discharge nozzle 11, as well as by the configuration of the nozzle 13, especially the speed, the utilized gas, as well as the pressure in the atomizing zone 3.

The gas supplied through the nozzles 12 and 13 can be the same gas, or it may consist of various gas mixtures. Preferably however, the same gas is always used. In addition it is also feasible with the inventive utilization of the hot gas atomizer apparatus to facilitate the hot gas atomization at a gas temperature of more than 1000K, preferably 1273K at an admission pressure of 0.1 to 6 MPa. At room temperature a gas speed of approximately 180 m/s occurs as a rule in the atomizing zone 3 at an admission pressure of 0.55 Mpa, while this can reach up to 250 m/s at 1073 K. In accordance with an especially advantageous arrangement the glass melt is brought to a maximum temperature of 1800 K in the melting device whereby due to gravity it then flows through the so-called platinum guide tube to the atomizer nozzle 11. According to one design example the inside diameter of this guide tube measures preferably 5 mm. The melt then drops into the atomizing zone 3 and is atomized by the gas flow of the second nozzle 13. In addition to providing directive function the gas flow of the first nozzle 12 is used to prevent return of droplets or fibers into the atomizing zone 3 and in addition to avoid wetting and clogging of the guide tube and the atomizer nozzle 11. The pressure in the first nozzle 12 is kept at 0.15-0.2 Megapascal. The temperature of the atomizing gas is adjustable. Droplets or fibers which are created by atomization are transported approximately 1 m in the spray tower and are subsequently cooled by appropriate ways as already described—cold gas or spray water. The resulting particles are removed. Particles from the gas flow are then transported with the gas flow into the cyclone 18 where they are discharged. In order to achieve the greatest possible number was well as fine fibers it has been demonstrated that the temperature of the glass melt 9 must be as high as possible already at the time of the particle formation, while the temperature in the atomizing area can then be very low and that the associated prevailing pressures are manageable. Table 1 below illustrates examples of variations of the individual process parameters for the utilization of the hot gas atomizer apparatus 1, whereby the individual variations 1 through 5 are consecutively numbered while the temperature of the glass melt 9, as well as the temperature of the gas which is to be supplied through the nozzles 12 and 13, and the pressure in the atomization zone 3 have been varied.

TABLE 1

Process Parameters of trials

| Trial Run # | Temperature of Melt | Atomizing Gas, $N_2$ Temperature, K | Pressure MPa | Quenching Water, l/h |
|---|---|---|---|---|
| 1 | 1673 | 753 | 0.34 | 50 |
| 2 | 1673 | 1223 | 0.34 | 100 |
| 3 | 1473 | 293 | 0.4 | 0 |
| 4 | 1573 | 293 | 0.4 | 0 |
| 5 | 1743 | 293 | 0.4 | 0 |

FIG. 5*a* shows an REM picture of the fibers from a method with the process parameters from experiment 3. FIG. 5*b* shows the REM picture of the fibers from variation 4, and FIG. 5*c* shows the REM picture of the fibers with variations of the process parameters according to experiment 5. It can be seen that the fiber diameter reduces considerably with varying melting temperatures during cold gas atomization as illustrated in the trials 4 and 5 which in turn leads to a finer breakdown and better fiber formation and thereby larger surface formation. The result of this is that atomization of a glass melt at very high temperature of same and thereby very low viscosity with cold gas is selected as an especially preferred method for particle formation. This offers the additional advantage that the cooling effect can be considerably reduced. Especially quenching in a water bath results partially in that cooling can largely be dispensed with.

Examples of possible compositions for biologically active glass powders with essentially non-spherical particles are given in Table 2, below, without however being limited to these ("Eg." in Table 2 means "example").

TABLE 2

Glass Compositions:

| Composition (weight %) | Eg. 1 | Eg. 2 | Eg. 3 | Eg. 4 | Eg. 5 | Eg. 6 | Eg. 7 | Eg. 8 | Eg. 9 | Eg. 10 | Eg. 11 | Eg. 12 |
|---|---|---|---|---|---|---|---|---|---|---|---|---|
| SiO2 | 45.00 | | | 63.40 | | 61.00 | 4.00 | | 35.00 | | | |
| Na2O | 24.50 | 11.90 | | 5.80 | 6.60 | | | 12.50 | 29.50 | 6.60 | 6.50 | 14.60 |
| Li2O | | | | | 1.60 | | | | | 1.60 | 1.60 | |
| K2O | | | | | 7.40 | | | | | 7.40 | 7.40 | |
| CaO | 24.50 | | 11.90 | | 1.00 | | 3.00 | 7.50 | 29.50 | 1.00 | 2.00 | 3.30 |
| MgO | | | | | | | 15.00 | | | | | |
| P2O5 | 6.00 | 66.90 | 65.90 | | 31.70 | | 69.00 | 66.30 | 6.00 | 31.70 | 31.70 | 33.50 |
| B2O3 | | | | 29.80 | | 37.00 | | | | | | |
| Al2O3 | | 6.20 | 6.20 | | | | 6.00 | 6.20 | | | | |
| SO3 | | | | | | | | | | 18.50 | 18.50 | 15.10 |
| Ag2O | | | 1.00 | | | 2.00 | 2.00 | | | 1.00 | | |
| SO3 | | | | | 18.50 | | | | | | | |
| TiO2 | | | | | | | 1.00 | | | | | |
| ZnO | | 15.00 | 16.00 | | 33.20 | | | 7.50 | | 32.20 | 32.30 | 33.50 |
| Sum | | 100.00 | 100.00 | 100.00 | 100.00 | 100.00 | 100.00 | 100.00 | 100.00 | 100.00 | 100.00 | 100.00 |
| Consistency (g/cm3) | | 2.7989 | | 2.204 | 3.0733 | | | 2.7349 | | | | |
| Alpha (20° C.; 300° C.)(1e−6/K) | | 12.71 | | 4.48 | 17.29 | 4.03 | 8.39 | 12.83 | | | | |
| Tg (° C.) | 521 | 352 | | 466 | 253 | 387 | 538 | 369 | | 253 | 265 | 390 |
| VA (TEMP at 1e4 dPas)(° C.) | 811 | 562 | | 953 | 419 | 1177 | | 592 | 1248 | 350 | 373 | |
| Temp at 1e7.6 dPas (° C.) | | 432 | | | 319 | | | 463 | | | | |
| Temp at 1e13 dPas (° C.) | | 354 | | | 257 | | | 382 | | | | |
| Tg—VA | 290 | 210 | | 487 | 166 | 790 | | 223 | | 97 | 108 | |

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

| | Component Identification |
|---|---|
| 1 | Hot gas atomizer apparatus |
| 2 | Melting zone |
| 3 | Atomizing zone |
| 4 | Cooling zone |
| 5 | Separation zone |
| 6 | Melting device |
| 7 | Receptacle for the biologically active glass |
| 8 | Heating device |
| 9 | Glass melt |
| 10 | Atomizer device |
| 11 | Discharge nozzle |
| 12 | Nozzle |
| 13 | Nozzle |
| 14 | Guiding device |
| 15 | Gas supply device |
| 16 | Device to pre-heat the gas |
| 17 | Gas tank |
| 18 | Separation device |
| 19 | Grinding device |
| 20 | Gravity atomizer |
| 21 | Annular gap |

The invention claimed is:

1. A method to produce biologically active glass powder comprising the following steps:

producing a glass melt from a predefined volume of glass;

forming a plurality of particles from said glass melt by atomizing, said plurality of particles including a plurality of non-spherical particles individual ones of which have a ratio of length to diameter of 1.1 to $10^5$, the biologically active glass powder including a higher than 90% content of said plurality of non-spherical particles, a particle geometry of said plurality of particles being influenced by synchronization of a first plurality of process parameters, said atomizing being established by a second plurality of process parameters in an atomization zone determined by a temperature of a supplied gas and a plurality of prevailing pressure conditions;

atomizing said glass melt in an atomizer apparatus to which said glass melt is supplied and which includes a first nozzle device and a second nozzle device which are located in tandem in a flow direction of said glass melt stream of said glass melt, at least one primary gas flow being admitted using said first nozzle device which discharges parallel to said glass melt stream in an area of entry of said glass melt stream into said atomizer apparatus and which guides said glass melt stream, a second gas flow being admitted for atomizing using a second nozzle device at an angle upon said glass melt stream, said second gas flow being admitted uniformly in a circumferential direction of said glass melt using said second nozzle device;

heating a gas which is to be supplied through said first and said second nozzle devices to a temperature of between 293 and 1300K; and admitting said gas which is to be supplied through said first and said second nozzle devices into said atomizer apparatus at a pressure of between 0.1 and 0.6 MPa.

2. The method in accordance with claim 1, wherein said glass melt is produced from said predefined volume of glass with one of a first composition and a second composition, said first composition including:

| | | |
|---|---|---|
| SiO$_2$ | 40-70 | weight % |
| P$_2$O$_5$ | 2-15 | weight % |
| Na$_2$O | 0-35 | weight % |
| CaO | 5-35 | weight % |
| MgO | 0-15 | weight % |
| F | 0-10 | weight %, | said second composition including:

| | | |
|---|---|---|
| P$_2$O$_5$ | 0-80 | weight % |
| SO$_3$ | 0-40 | weight % |
| B$_2$O$_3$ | 0-50 | weight % |
| Al$_2$O$_3$ | 0-10 | weight % |
| SiO$_2$ | 0-10 | weight % |
| Li$_2$O | 0-25 | weight % |
| Na$_2$O | 0-20 | weight % |
| K$_2$O | 0-25 | weight % |
| CaO | 0-25 | weight % |
| MgO | 0-15 | weight % |
| SrO | 0-15 | weight % |
| BaO | 0-15 | weight % |
| ZnO | 0-25 | weight % |
| Ag$_2$O | 0-5 | weight % |
| CuO | 0-10 | weight % |
| GeO$_2$ | 0-10 | weight % |
| TeO$_2$ | 0-15 | weight % |
| Cr$_2$O$_3$ | 0-10 | weight % |
| J | 0-10 | weight %, | wherein in said second composition a sum SiO$_2$+P$_2$O$_5$+B$_2$O$_3$+Al$_2$O$_3$ amounts to between 30-80 weight %, a sum ZnO+Ag$_2$O+CuO+GeO$_2$+TeO$_2$+Cr$_2$O$_3$+J amounts to 0.1-40 weight %, and a sum R$^1_2$O+R$^2$O amounts to 0.1-60% weight, R$^1$ being an alkali metal, and R$^2$ being an earth alkali metal.

3. The method in accordance with claim 1, wherein subsequent to said heating and admitting steps, said plurality of particles are ground to more than 90% non-spherical particles with a particle size having a ratio of length to diameter which is 1.1 to $10^5$.

4. The method in accordance with claim 1, wherein subsequent to said heating and admitting steps, said plurality of particles are ground to more than 90% non-spherical particles with a particle size having a ratio of length to diameter which is 100 to $10^4$.

5. The method in accordance with claim 1, wherein subsequent to said heating and admitting steps, said plurality of particles are ground to more than 90% non-spherical particles with a particle size having a ratio of length to diameter which is 10 to $10^4$.

6. The method in accordance with claim 1, wherein said glass melt is heated to a temperature of between 1400 and 1800 K.

7. The method in accordance with claim 1, wherein said glass melt is heated to a temperature of between 1600 and 1800 K.

8. The method in accordance with claim 1, wherein said second gas flow is admitted at an angle of between 20 to 60°.

9. The method in accordance with claim 1, wherein said first and said second nozzle devices are supplied with said gas having a same third plurality of process parameters.

10. The method in accordance with claim 1, wherein said gas which is to be supplied through said first and said second nozzle devices is an inert gas.

11. The method in accordance with claim 1, further comprising the step of quenching in a cooling zone said plurality of particles which are formed from said glass melt.

12. The method in accordance with claim 11, wherein said quenching occurs through admitting one of a gas and a bath.

13. The method in accordance with claim 1, wherein said atomizer apparatus is a hot gas atomizer apparatus.

14. The method in accordance with claim 1, further comprising the step of grinding said plurality of particles which are formed from said glass melt, said grinding occurring with a medium.

15. The method in accordance with claim 1, wherein individual ones of said plurality of non-spherical particles have a length of 1 μm to $10^5$ μm and a diameter in a range of 0.5 μm to 10 μm.

16. The method in accordance with claim 1, wherein individual ones of said plurality of non-spherical particles have a length of 1 μm to $10^5$ μm and a diameter in a range of 0.5 μm to 2 μm.

17. The method in accordance with claim 1, wherein individual ones of said plurality of non-spherical particles have a length of 10 μm to $10^4$ μm and a diameter in a range of 0.5 μm to 10 μm.

18. The method in accordance with claim 1, wherein individual ones of said plurality of non-spherical particles have a length of 10 μm to $10^4$ μm and a diameter in a range 0.5 μm to 2 μm.

19. The method in accordance with claim 1, wherein individual ones of said plurality of non-spherical particles have a length of 100 μm to $10^4$ μm and a diameter in a range of 0.5 μm to 10 μm.

20. The method in accordance with claim 1, wherein individual ones of said plurality of non-spherical particles have a length of 100 μm to $10^4$ μm and a diameter in a range of 0.5 μm to 2 μm.

* * * * *

UNITED STATES PATENT AND TRADEMARK OFFICE
CERTIFICATE OF CORRECTION

| | | |
|---|---|---|
| PATENT NO. | : 7,905,115 B2 | Page 1 of 1 |
| APPLICATION NO. | : 11/813449 | |
| DATED | : March 15, 2011 | |
| INVENTOR(S) | : Guido Rake et al. | |

It is certified that error appears in the above-identified patent and that said Letters Patent is hereby corrected as shown below:

COLUMN 10
    At line 19, please delete "possible number was", and substitute therefore --possible number as--.

Signed and Sealed this
Sixth Day of December, 2011

David J. Kappos
*Director of the United States Patent and Trademark Office*